(12) United States Patent
Marcus (10) Patent No.: US 12,168,055 B2
(45) Date of Patent: Dec. 17, 2024

(54) SONOSENSITIZATION

(71) Applicant: SONALASENSE, INC., Berkeley, CA (US)

(72) Inventor: Stuart L. Marcus, Berkeley, CA (US)

(73) Assignee: SonalaSense, Inc., Berkeley, CA (US)

( * ) Notice: Subject to any disclaimer, the term of this patent is extended or adjusted under 35 U.S.C. 154(b) by 0 days.

(21) Appl. No.: 18/584,620

(22) Filed: Feb. 22, 2024

(65) Prior Publication Data

US 2024/0189427 A1 Jun. 13, 2024

Related U.S. Application Data

(63) Continuation of application No. 17/613,788, filed as application No. PCT/US2020/034944 on May 28, 2020.

(60) Provisional application No. 62/853,853, filed on May 29, 2019.

(51) Int. Cl.
| | |
|---|---|
| *A61K 41/00* | (2020.01) |
| *A61K 9/00* | (2006.01) |
| *A61K 31/197* | (2006.01) |
| *A61M 37/00* | (2006.01) |
| *A61N 7/00* | (2006.01) |
| *A61P 35/00* | (2006.01) |

(52) U.S. Cl.
CPC ........ *A61K 41/0033* (2013.01); *A61K 9/0019* (2013.01); *A61K 31/197* (2013.01); *A61M 37/0092* (2013.01); *A61N 7/00* (2013.01); *A61P 35/00* (2018.01); *A61M 2205/6054* (2013.01); *A61N 2007/0039* (2013.01)

(58) Field of Classification Search
CPC .............. A61K 41/0033; A61K 9/0019; A61K 31/197; A61M 37/0092; A61M 2205/6054; A61N 7/00; A61N 2007/0039; A61P 35/00
See application file for complete search history.

(56) References Cited

U.S. PATENT DOCUMENTS

| | | |
|---|---|---|
| 4,576,177 A | 3/1986 | Webster, Jr. |
| 4,735,201 A | 4/1988 | Oreilly |
| 4,807,633 A | 2/1989 | Fry |
| 4,875,487 A | 10/1989 | Seppi |
| 5,344,974 A | 9/1994 | Descotes et al. |
| 5,733,770 A | 3/1998 | Watanabe et al. |
| 5,738,635 A | 4/1998 | Chapelon et al. |
| 5,817,048 A | 10/1998 | Lawandy |

(Continued)

FOREIGN PATENT DOCUMENTS

| | | |
|---|---|---|
| CN | 102885648 A | 1/2013 |
| CN | 211536251 U | 9/2020 |

(Continued)

OTHER PUBLICATIONS

Wood, et al. "A Review of Low Intensity Ultrasound for Cancer Therapy." Ultrasound in Med. & Bio.,., vol. 41, No. 4, pp. 905-928, 2015 (Year: 2015).*

(Continued)

*Primary Examiner* — Amber R Stiles
(74) *Attorney, Agent, or Firm* — Mintz, Levin, Cohn, Ferris, Glovsky and Popeo, P.C.

(57) ABSTRACT

An improved method for MRI-guided sonosensitized focused ultrasound treatment of malignant tissue is disclosed herein.

29 Claims, 1 Drawing Sheet

(56) References Cited

U.S. PATENT DOCUMENTS

| | | |
|---|---|---|
| 6,335,465 B1 * | 1/2002 | Golub ............... C07C 227/42 |
| | | 562/567 |
| 6,428,968 B1 | 8/2002 | Molnar-kimber et al. |
| 6,498,945 B1 | 12/2002 | Alfheim et al. |
| 6,572,839 B2 | 6/2003 | Sugita et al. |
| 6,575,922 B1 | 6/2003 | Fearnside et al. |
| 6,576,257 B1 | 6/2003 | Yarmut |
| 6,622,049 B2 | 9/2003 | Penner et al. |
| 6,669,687 B1 | 12/2003 | Saadat |
| 6,723,750 B2 | 4/2004 | Voet |
| 6,733,450 B1 | 5/2004 | Alexandrov et al. |
| 6,905,671 B1 | 6/2005 | Tanaka et al. |
| 7,018,395 B2 | 3/2006 | Chen |
| 7,125,387 B2 | 10/2006 | Kawabata et al. |
| 7,252,677 B2 | 8/2007 | Burwell et al. |
| 7,498,029 B2 | 3/2009 | Hasan et al. |
| 7,514,069 B2 | 4/2009 | Achilefu et al. |
| 7,652,410 B2 | 1/2010 | Prus |
| 7,713,203 B2 | 5/2010 | Lacoste et al. |
| 7,790,144 B2 | 9/2010 | Achilefu et al. |
| 7,888,626 B2 | 2/2011 | Slinger et al. |
| 8,002,706 B2 | 8/2011 | Vortman et al. |
| 8,070,682 B2 | 12/2011 | Zhu |
| 8,123,789 B2 | 2/2012 | Khanna |
| 8,173,839 B2 | 5/2012 | Tachiya et al. |
| 8,198,325 B2 | 6/2012 | Oh et al. |
| 8,206,326 B2 | 6/2012 | Schafer et al. |
| 8,318,133 B2 | 11/2012 | Achilefu et al. |
| 8,409,099 B2 | 4/2013 | Vitek et al. |
| 8,492,578 B2 | 7/2013 | Glanzmann et al. |
| 8,548,561 B2 | 10/2013 | Vortman et al. |
| 8,548,562 B2 | 10/2013 | Trachtenberg et al. |
| 8,574,174 B2 | 11/2013 | Schafer et al. |
| 8,617,073 B2 | 12/2013 | Prus et al. |
| 8,741,262 B2 | 6/2014 | Ni et al. |
| 8,758,725 B2 | 6/2014 | Sharma et al. |
| 8,770,203 B2 | 7/2014 | Bourke et al. |
| 8,771,741 B2 | 7/2014 | Adair et al. |
| 8,979,775 B2 | 3/2015 | Schafer et al. |
| 8,992,958 B2 | 3/2015 | Kanehira et al. |
| 9,012,502 B2 | 4/2015 | Chibazakura et al. |
| 9,023,090 B2 | 5/2015 | Palti |
| 9,072,774 B2 | 7/2015 | Zheng et al. |
| 9,249,086 B2 | 2/2016 | Brænden et al. |
| 9,313,423 B2 | 4/2016 | Wang et al. |
| 9,326,964 B2 | 5/2016 | Stensrud |
| 9,371,555 B2 | 6/2016 | Roberts |
| 9,412,357 B2 | 8/2016 | Medan et al. |
| 9,463,256 B2 | 10/2016 | Lub et al. |
| 9,475,028 B2 | 10/2016 | Krishna et al. |
| 9,492,121 B2 | 11/2016 | Andrews et al. |
| 9,492,681 B2 | 11/2016 | Aydt et al. |
| 9,493,810 B2 | 11/2016 | Ezrin |
| 9,498,650 B2 | 11/2016 | Schafer et al. |
| 9,510,909 B2 | 12/2016 | Grant et al. |
| 9,572,880 B2 | 2/2017 | Harris et al. |
| 9,764,029 B2 | 9/2017 | Shibaguchi et al. |
| 9,816,118 B2 | 11/2017 | Lee et al. |
| 9,833,634 B2 | 12/2017 | Bourke et al. |
| 9,963,724 B2 | 5/2018 | Saito et al. |
| 9,974,974 B2 | 5/2018 | Groseth |
| 10,130,828 B2 | 11/2018 | Vortman et al. |
| 10,272,008 B2 | 4/2019 | Zwierstra et al. |
| 10,456,603 B2 | 10/2019 | Tlusty et al. |
| 10,555,861 B2 | 2/2020 | Zwierstra et al. |
| 10,653,653 B2 | 5/2020 | Zhao et al. |
| 10,675,482 B2 | 6/2020 | Agarwal et al. |
| 10,702,244 B2 | 7/2020 | O'reilly et al. |
| 10,773,098 B2 | 9/2020 | Liu et al. |
| 11,318,332 B2 | 5/2022 | Agarwal et al. |
| 11,491,353 B2 | 11/2022 | Agarwal et al. |
| 11,617,904 B2 | 4/2023 | Agarwal et al. |
| 2001/0002251 A1 | 5/2001 | Woodburn et al. |
| 2001/0041163 A1 | 11/2001 | Sugita et al. |
| 2003/0114434 A1 | 6/2003 | Chen et al. |
| 2004/0171601 A1 | 9/2004 | Fukumura et al. |
| 2005/0060012 A1 | 3/2005 | Voorhees et al. |
| 2005/0277824 A1 | 12/2005 | Aubry et al. |
| 2006/0020310 A1 | 1/2006 | Loebel et al. |
| 2007/0005121 A1 | 1/2007 | Khanna |
| 2007/0038099 A1 | 2/2007 | Sugita et al. |
| 2007/0260295 A1 | 11/2007 | Chen et al. |
| 2009/0062724 A1 | 3/2009 | Chen |
| 2009/0062752 A1 | 3/2009 | Gonnelli |
| 2009/0275548 A1 | 11/2009 | Lewis et al. |
| 2010/0217160 A1 | 8/2010 | Saguchi et al. |
| 2010/0262115 A1 | 10/2010 | Madiyalakan et al. |
| 2012/0016429 A1 | 1/2012 | Klorg |
| 2012/0089205 A1 | 4/2012 | Boyden et al. |
| 2012/0271167 A1 | 10/2012 | Holland et al. |
| 2012/0283605 A1 | 11/2012 | Lewis, Jr. |
| 2014/0039309 A1 | 2/2014 | Harris et al. |
| 2016/0325110 A1 | 11/2016 | Agarwal et al. |
| 2017/0173351 A1 | 6/2017 | Agarwal et al. |
| 2018/0049762 A1 | 2/2018 | Seip et al. |
| 2018/0177491 A1 | 6/2018 | Hynynen et al. |
| 2018/0207447 A1 | 7/2018 | Liu et al. |
| 2018/0344849 A1 | 12/2018 | Trouard et al. |
| 2019/0009109 A1 | 1/2019 | Vortman et al. |
| 2019/0009111 A1 | 1/2019 | Myhr et al. |
| 2019/0021666 A1 | 1/2019 | Hynynen |
| 2019/0070296 A1 | 3/2019 | Wang et al. |
| 2019/0175433 A1 | 6/2019 | Zwierstra et al. |
| 2019/0307427 A1 | 10/2019 | Levy et al. |
| 2020/0124607 A1 | 4/2020 | Ezrin |
| 2020/0146917 A1 | 5/2020 | Zwierstra et al. |
| 2021/0008385 A1 | 1/2021 | Agarwal et al. |
| 2022/0226471 A1 * | 7/2022 | Marcus ............... A61B 5/4848 |

FOREIGN PATENT DOCUMENTS

| | | |
|---|---|---|
| EP | 1909908 B1 | 3/2011 |
| GB | 2343186 A | 5/2000 |
| JP | S6053131 A | 3/1985 |
| JP | S62202813 U | 12/1987 |
| JP | 2005125075 A | 5/2005 |
| JP | 2005152093 A | 6/2005 |
| JP | 2011509737 A | 3/2011 |
| JP | 2011-225471 A | 11/2011 |
| JP | 2012-012305 A | 1/2012 |
| JP | 2015-214524 A | 12/2015 |
| WO | 8705297 A1 | 9/1987 |
| WO | 9210142 A1 | 6/1992 |
| WO | 9505214 A1 | 2/1995 |
| WO | 9628200 A1 | 9/1996 |
| WO | 9852610 A1 | 11/1998 |
| WO | 2009026724 A1 | 3/2009 |
| WO | 2009095912 A1 | 8/2009 |
| WO | 2012035747 A1 | 3/2012 |
| WO | 2018026738 A1 | 2/2018 |
| WO | 2018035256 A1 | 2/2018 |
| WO | 2018112664 A1 | 6/2018 |
| WO | 2019059027 A1 | 3/2019 |
| WO | 2020033764 A1 | 2/2020 |
| WO | 2020167992 A1 | 8/2020 |
| WO | 2020217472 A1 | 10/2020 |
| WO | 2020243319 A1 | 12/2020 |
| WO | 2021154730 A1 | 8/2021 |

OTHER PUBLICATIONS

Yoshida et al., "Sonodynamic Therapy for Malignant Glioma Using 220 KHz Transcranial Magnetic Resonance Imaging-Guided Focused Ultrasound and 5-Aminolevulinic Acid", Ultrasound in Med. & Biol.., vol. 00, No.., p. 1-13, 2018 (Year: 2018).*

Ohmura et al., "Sonodynamic Therapy with 5-Aminolevulinic Acid and Focused Ultrasound for Deep-seated Intracranial Glioma in Rat", Anticancer Research, 31: 2527-2534 (2011). (Year: 2011).*

Ohmura et al., "Sonodynamic Therapy with 5-Aminolevulinic Acid and Focused Ultrasound for Deep-seated Intracranial Giloma in Rat", ANticancer Research, 31: 2527-2534. (Year: 2011).*

SONALASENSE, Inc. (Dec. 26, 2023) "A Phase 2 Study of (56) References Cited

OTHER PUBLICATIONS

Sonodynamic Therapy Using SONALA-001 and Exablate 4000 Type 2.0 in Patients With DIPG", ClinicalTrials.gov, 1-15.
(May 7, 2023) "ECOG Performance Status (WHO/GOG/Zubrod score)", Performance status|HemOnc.org—A Hematology Oncology Wiki, 4 pages.
European Search Report issued in European Application No. 20813875.0, mailed on Sep. 7, 2023, 11 pages.
(Nov. 14, 2023) "FDA Grants Fast Track Designation to SonALAsense's SONALA-001 in Combination with the INSIGHTEC Transcranial Ultrasound Device for Sonodynamic Therapy of DIPG, a Rare Pediatric Brain Cancer", SONALASENSE, 4 pages.
Diamond et al. (Dec. 2, 1972) "Photodynamic Therapy of Malignant Tumours", The Lancet, 300(7788):1175-1177.
Dijkmans et al. (2004) "Microbubbles and Ultrasound: From Diagnosis to Therapy", European Journal of Echocardiography, 5(4):245-256.
Farrukh et al. (Feb. 13, 2023), "Emerging Therapeutic Strategies for Diffuse Intrinsic Pontine Glioma: A Systematic Review", Healthcare (Basel), 11(4):559 (26 pages).
Fisher et al. (2017) "ALA-PpIX Mediated Photodynamic Therapy of Malignant Gliomas Augmented by Hypothermia", PLOS One, 12(7):e0181654 (20 pages).
Gomer et al. (Jan. 1979) "Determination of [3H]- and [14C]hematoporphyrin Derivative Distribution in Malignant and Normal Tissue", Cancer Research, 39(1):146-151.
Hirschberg et al. (2017), "Synergistic Efficacy of Ultrasound, Sonosensitizers and Chemotherapy: A Review", Therapeutic Delivery, 8(5):331-342.
Hynynen et al. (Apr. 2006) "Pre-Clinical Testing of a Phased Array Ultrasound System for MRI-Guided Noninvasive Surgery of the Brain—A Primate Study", European Journal of Radiology, 59(2):149-156.
International Search Report and Written Opinion received for PCT Application No. PCT/US2020/034944, mailed on Aug. 11, 2020, 9 pages.
Jain et al. (2018) "Ultrasound-Based Triggered Drug Delivery to Tumors", Drug Delivery and Translational Research, 8(1):150-164.
Jeong et al. (Dec. 2012) "Sonodynamically Induced Antitumor Effects of 5-aminolevulinic Acid and Fractionated Ultrasound Irradiation in an Orthotopic Rat Glioma Model", Ultrasound in Medicine and Biology, 38(12):2143-2150.
Kinoshita et al. (2006) "Mechanism of Porphyrin-Induced Sonodynamic Effect: Possible Role of Hyperthermia", Radiation Research, 165(3):299-306.
Kou et al. (Jan. 19, 2017) "Berberine-Sonodynamic Therapy Induces Autophagy and Lipid Unloading in Macrophage", Cell Death and Disease, 8(1):e2558 (12 pages).
Lee et al. (May 30, 2017) "Doxycycline Potentiates Antitumor Effect of 5-aminolevulinic Acid-mediated Photodynamic Therapy in Malignant Peripheral Nerve Sheath Tumor Cells", PLoS ONE, 12(5):e0178493(18 pages).
Li et al. (Jul. 10, 2015) "5-Aminolevulinic Acid-Based Sonodynamic Therapy Induces the Apoptosis of Osteosarcoma in Mice", PLoS One, 10(7):e0132074 (16 pages).
Maytin et al. (Sep. 2012) "Vitamin D Combined with Aminolevulinate (ALA)-Mediated Photodynamic Therapy (PDT) for Human Psoriasis: A Proof-of-Principle Study", Israel Journal of Chemistry, 52(8-9):767-775.
McDannold et al.(2010) "Transcranial Magnetic Resonance Imaging-Guided Focused Ultrasound Surgery of Brain Tumors: Initial Findings in 3 Patients", Neurosurgery, 66(2):323-332.
Nonaka et al. (Mar. 2009) "Sonodynamic Therapy Consisting of Focused Ultrasound and a Photosensitizer Causes a Selective Antitumor Effect in a Rat Intracranial Glioma Model", Anticancer research, 29(3):943-950.

Ohmura et al. (2011) "Sonodynamic Therapy with 5-Aminolevulinic Acid and Focused Ultrasound for Deep-Seated Intracranial Glioma in Rat", Anticancer Research, 31(7):2527-2534.
Ore et al. (2023) "Advances and Clinical Trials Update in the Treatment of Diffuse Intrinsic Pontine Gliomas", Pediatric Neurosurgery, 58(5):259-266.
Osaki et al. (2016) "Sonodynamic Therapy Using 5-aminolevulinic Acid Enhances the Efficacy of Bleomycin", Ultrasonics, 67:76-84.
Perotti et al. (Mar. 16, 2004) "Porphyrin Synthesis from ALA Derivatives for Photodynamic Therapy. In Vitro and in Vivo Studies", British Journal of Cancer, 90:1660-1665.
Sanai et al. (Nov. 16-20, 2022) "A First-in-Human Phase 0/1 Trial of 5-Aminolevulinic Acid Sonodynamic Therapy (5-ALA SDT) in Recurrent Glioblastoma", 2022 Society for Neuro-Oncology's 27th Annual Scientific Meeting and Education Day, Tampa Bay, FL USA, Abstract CTNI-13, 72-73.
Shimamura et al. (2016) "5-aminolevulinic Acid Enhances Ultrasound-mediated Antitumor Activity via Mitochondrial Oxidative Damage in Breast Cancer", Anticancer Research, 36(7):3607-3612.
Song et al. (2011) "Apoptosis of SAS Cells Induced by Sonodynamic Therapy Using 5-Aminolevulinic Acid Sonosensitizer", Anticancer Research, 31:39-46.
Song et al. (2012) "Overview of Therapeutic Hypothermia", Current Treatment Options in Neurology, 14(6):541-548.
Stupp et al. (2005) "Radiotherapy plus Concomitant and Adjuvant Temozolomide for Glioblastoma", The New England Journal of Medicine, 352(10):987-996.
Suehiro et al. (Jan. 19, 2018) "Enhancement of Antitumor Activity by Using 5-ALA-mediated Sonodynamic Therapy to Induce Apoptosis in Malignant Gliomas: Significance of High-intensity Focused Ultrasound on 5-ALA-SDT in a Mouse Glioma Model", Journal of Neurosurgery, 129(6); 1416-1428.
Syed et al. (Apr. 2023) "First-in-Human Sonodynamic Therapy with ALA for Pediatric Diffuse Intrinsic Pontine Glioma: a Phase 1/2 Study using Low-Intensity Focused Ultrasound", Journal of Neuro-Oncology, 162(2):449-451.
Vansevičiūtė et al. (2014) "5-aminolevulinic Acid-based Fluorescence Diagnostics of Cervical Preinvasive Changes", Medicina, 50(3):137-143.
Wang et al. (2008) "Study of Cell Killing Effect on S180 by Ultrasound Activating Protoporphyrin IX", Ultrasonics, 48(2):135-140.
Warren, Katherine E. (Dec. 28, 2012) "Diffuse Intrinsic Pontine Glioma: Poised for Progress", Frontiers in Oncology, 2(205):1-9.
Wood et al. (2015) "A Review of Low-Intensity Ultrasound for Cancer Therapy", Ultrasound in Medicine and Biology, 41(4):905-928.
Wu et al. (Jul. 18, 2019) "MR-guided Focused Ultrasound Facilitates Sonodynamic Therapy with 5-Aminolevulinic Acid in a Rat Glioma Model", Scientific Reports, 9(1): 10465(pp. 1-10).
Yang et al. (2014) "Methotrexate Enhances 5-aminolevulinic Acid-mediated Photodynamic Therapy-induced Killing of Human SCC4 Cells by Upregulation of Coproporphyrinogen Oxidase", Journal of the Formosan Medical Association, 113(2):88-93.
Yoshida et al. (2018) "Sonodynamic Therapy for Malignant Glioma Using 220-kHz Transcranial Magnetic Resonance Imaging-guided Focused Ultrasound and 5-aminolevulinic Acid", Ultrasound in Medicine and Biology, 45(2):526-538.
Yumita et al. (Mar. 1989) "Hematoporphyrin as a Sensitizer of Cell-damaging Effect of Ultrasound", Japanese Journal of Cancer Research, 80(3):219-222.
Yumita et al. (Sep. 2004) "Sonodynamic Therapy on Chemically Induced Mammary Tumor: Pharmacokinetics, Tissue Distribution and Sonodynamically Induced Antitumor Effect of Porfimer Sodium", Cancer Science, 95(9):765-769.
Zhang et al. (Mar. 2018) "An Updated Overview on the Development of New Photosensitizers for Anticancer Photodynamic Therapy", Acta Pharmaceutica Sinica B, 8(2):137-146.

* cited by examiner

SONOSENSITIZATION

CROSS-REFERENCES TO RELATED APPLICATIONS

This application is a Continuation of U.S. application Ser. No. 17/613,788, filed Nov. 23, 2021, which is a U.S. National Phase Application of PCT International Application No. PCT/US2020/034944, filed May 28, 2020, which is an International Application of and claims the benefit of priority to U.S. Provisional Patent Application No. 62/853,853, filed on May 29, 2019, the entire contents of which are herein incorporated by reference.

FIELD

The disclosures provided herein relate generally to medical treatments. More particularly, the disclosures relate to medical treatments using ultrasound and an ultrasound sensitizer.

BACKGROUND

Hematoporphyrins and their derivatives were described as accumulating preferentially in tumor cells in 1942 (H. Auler et al., *Z. Krebsforsch.* (1942) 53:65-68). The fluorescent property of the compound is employed to mark tumor tissue, as a surgical aid and as a diagnostic (R. Vansevičitė et al., *Medicina* (2014) 50:137-43; J. Zhang et al., *Acta Pharm Sinica* B (2018) 8:137-46). In 1972, it was demonstrated that hematoporphyrins could be used to selectively sensitize tumor cells to light in the presence of oxygen (the "photodynamic effect"), resulting in reduction in size of the tumor, a procedure now known as photodynamic therapy (I. Diamond et al., *Lancet* (1972) 2:1175-77). Hematoporphyrins in most organisms are converted to heme and related molecules. It is believed that hematoporphyrins accumulate in certain tumor tissues due to lack of iron, or dysfunction of metabolic enzymes (W. Song et al., *Anticancer Res* (2011) 31:39-46; C. J. Gomer et al., *Cancer Res* (1979) 39:146-51). This permits the selective destruction of tumor cells using light, leaving healthy nearby tissue relatively unaffected. It was also discovered that when one administers exogenous 5-aminolevulinic acid ("5-ALA"), the first committed molecule in the heme pathway, the photosensitizing porphyrin protoporphyrin-IX accumulates and allows tissue photosensitization within a few hours (C. Perotti et al., *Br J Cancer* (2004) 90:1660-65). Photodynamic therapy, however, is limited by the opacity of tissue: effective treatment tumors not accessible from the body surface or lumen can require surgical access to the tumor site.

Sonodynamic therapy ("SDT") is a method for destroying cells using focused ultrasound (FUS) after sensitization with a sonosensitizer. The mechanism of action has not been conclusively determined, but is believed to be due to thermal effects and/or singlet oxygen produced by cavitation. Ultrasound is capable of penetrating tissue to a far greater distance than light, making more of the body accessible to non-invasive treatment. Surprisingly, it was discovered that protoporphyrin-IX is also an effective sonosensitizer (N. Yumita et al., *Jpn J Cancer Res* (1989) 80(3):219-22), enabling the destruction of cells by ultrasound under conditions that would otherwise be ineffective. Again, the mechanism of action is unclear, but has been hypothesized to result from singlet oxygen formation.

To date, there are a number of reported in vitro and in vivo experiments, but no clinical trial results (H. Hirschberg et al., *Ther Deliv* (2017) 8:331-42). For example, N. Yumita et al., supra, investigated the effect of SDT on mouse sarcoma 180 or rat ascites hepatoma 130 cells in vitro, using hematoporphyrin (10, 25, or 50 µg/mL) and ultrasound (1.92 MHz) at intensities of 1.27, 2.21 or 3.18 W/cm$^2$, for a duration of 15, 30 or 60 seconds. Hematoporphyrin was applied to the cells 15, 30, or 60 seconds before ultrasound application. Yumita reported that 60 seconds of ultrasound alone damaged a significant number of cells (16% and 17% for sarcoma 180 and ascites hepatoma, respectively), as determined by trypan blue dye exclusion. A larger number of cells were damaged at the higher intensities (2.21 W/cm$^2$: 71% and 75%; 3.18 W/cm$^2$: 79% and 86%). When hematoporphyrin was added (50 µg/mL), substantially more sarcoma cells were damaged after exposure to 1.27 or 3.18 W/cm$^2$ (67% and 98%), while more AH cells were damaged at 2.21 and 3.18 W/cm$^2$ (95% and 96%). Statistically significant cell damage was also reported using hematoporphyrin at 25 µg/mL with ultrasound intensity at 3.18 W/cm$^2$ (98% and 96%), equivalent to the cell destruction using 50 µg/mL.

N. Yumita et al., *Cancer Sci* (2004) 95:765-69, reported treating female Sprague-Dawley rats with mammary tumors (induced by injection of 7,12-dimethylbenz(a)anthracene) with porfimer sodium (0, 0.5, 1.0, 2.5, or 5 mg/kg, i.v. 24 hours before ultrasound) and ultrasound at 1.92 MHz for 15 minutes at intensities of 1, 2, 3, or 5 W/cm$^2$. Yumita reported that SDT treatment with porfimer sodium (2.5 mg/kg or higher) and ultrasound (3 W/cm$^2$ or higher) effectively inhibited tumor growth, and that the higher treatment levels (5 mg/kg at 3 W/cm$^2$, or 2.5 mg/kg at 5 W/cm$^2$) were not significantly different from treatment with 2.5 mg/kg at 3 W/cm$^2$.

W. Song et al., supra, investigated the reaction of SAS cells in vitro, using 5-ALA (1, 10, or 50 µg/mL) applied 4 hours before ultrasound application, 1.05 MHz with a duty cycle of 60%, a pulse repetition frequency of 100 Hz, for a 2 min duration, intensity approximately 2 W/cm$^2$. Song reported cell viability of 89%, 88%, 75%, and 62% (for 0, 1, 10, and 50 µg/mL 5-ALA); the reduction in viability was statistically significant for 10 and 50 µg/mL. Song also reported that treatment with ultrasound increased SAS cell apoptosis, intracellular reactive oxygen species, and lipid peroxidation, and that addition of 10 µg/mL 5-ALA significantly increased these effects.

S. Suchiro et al., *J Neurosurg* (2018) 129:1416-28, reported in vitro studies with U87 and U251 glioma cells, and U251$^{Oct-3/4}$ glioma stem-like cells, using 5-ALA (1 mM) and ultrasound (3 MHz) at 2 W/cm$^2$, using a 20% duty cycle for 3 minutes. Suchiro reported that ultrasound alone destroyed U87 and U251$^{Oct-3/4}$ to a significant degree, but not U251 cells. Ultrasound in combination with 5-ALA (1 mM) was substantially cytotoxic to all tumor cells tested (but not to normal control cells), and significantly more effective than ultrasound alone in all three cases. Suchiro also used immunodeficient BALB/c nude mice injected with human U87 glioma cells or U251$^{Oct-3/4}$ glioma stem-like cells, treated with 5-ALA (100 mg/kg) and ultrasound (2.2 MHz, 0.5 or 2.0 W/cm$^2$, 20% duty cycle for 3 minutes), repeated weekly for 3 weeks. Suchiro reported that SDT treatment significantly improved the survival of treated mice.

J. Y. Kou et al., *Cell Death Dis* (2017) 8:e2558 reported in vitro studies on human THP-1 monocytes (induced to become macrophages and foam cells), using berberine as sonosensitizer (30 µg/mL), exposed to ultrasound (1.0 MHZ) at intensities 0.4 W/cm$^2$, for durations of 10 minutes (other concentrations, intensities, and durations were also tried, but not in combination). Kou reported that treatment induced autophagy in macrophages, and increased cholesterol efflux.

M. Nonaka et al., *Anticancer Res* (2009) 29:943-50, used C6 rat glioma cells injected into Wistar rats, and treated with Rose Bengal (50 mg/kg, i.v. 10 minutes before treatment) and ultrasound (1 MHz at 25 W/cm$^2$, for 5 minutes, with the transducer applied directly to the brain surface through a 10 mm craniotomy). Control groups lacking glioma cells were also tested at 0, 10 or 50 mg/kg Rose Bengal and ultrasound at 25 and 110 W/cm$^2$. Nonaka reported that rats with normal brain tissue showed no lesions at 25 W/cm$^2$, with or without Rose Bengal. Rats with normal brain tissue treated with ultrasound alone at 110 W/cm$^2$ for 3 minutes displayed coagulation necrosis in 2 out of 6 rats, and in 5 out of 6 rats treated for 5 minutes at that intensity. Rats treated with Rose Bengal (10 or 50 mg/kg) and ultrasound at 110 W/cm$^2$ for 3 minutes all displayed lesions (5/5 for each group). Rats treated with Rose Bengal (10 or 50 mg/kg) and ultrasound at 110 W/cm$^2$ for 5 minutes also displayed lesions (6/7 at 10 mg/kg; 6/6 at 50 mg/kg).

T. Ohmura et al., *Anticancer Res* (2011) 31:25274-33, used C6 rat glioma cells injected into Wistar rats, and treated with 5-ALA (100 mg/kg, administered orally 3 hours before ultrasound treatment) and ultrasound 1.04 MHz at 10 W/cm$^2$ for 5 minutes, with the ultrasound transducer applied directly to the brain surface through a 10 mm craniotomy. Rats with normal brain tissue were also treated with ultrasound at 1.04 MHz at 10, 15, 20, or 25 W/cm$^2$ for five minutes. Ohmura reported that rats with normal brain tissue that received ultrasound at 15, 20, or 25 W/cm$^2$ exhibited necrosis at the ultrasound focus region. Rats with glioma cells treated with SDT exhibited significantly smaller tumors than rats that received 5-ALA or ultrasound alone.

E-J Jeong et al., *Ultrasound Med Biol* (2012) 38:2143-50, used Sprague Dawley rats inoculated with C6 glioma cells, treated with 5-ALA (60 mg/kg) or Radachlorin (40 mg/kg); and ultrasound at 1.0 MHz, 2.65 W/cm$^2$ for 20 minutes (16 minutes of ultrasound, followed by a 3 minute break, followed by an additional 4 minutes of ultrasound). Jeong reported that rats receiving SDT exhibited tumors significantly smaller in size than the control groups.

Y Li et al., *PLOS One* (2015) 10:e0132074, used rat osteosarcoma UMR-106 cells in BALB/c nude mice, treated daily with 5-ALA (250 mg/kg i.v., 8 hours before ultrasound) and ultrasound at 1.0 MHz, 2.5 W/cm$^2$, 10% duty factor, pulse repetition at 100 Hz, for 8 minutes daily for 10 days. Li reported that mice receiving ultrasound alone exhibited small tumor volumes than controls or mice receiving only 5-ALA, and that mice receiving SDT exhibited smaller tumor volumes significantly smaller than all other groups.

Further advances in sonodynamic therapy have often focused on improving the sensitizer, increasing the selectivity for malignant tissue, the distribution throughout the body, or the sensitivity to ultrasound. Woodburn et al., US 20010002251, disclosed the use of texaphyrins as an SDT sensitizer. Sanderson et al., disclosed the use of tetrasulphamoylphthalocyanine and naphthalocyanine derivatives (GB 2343186), and tetra-sulphamoylphthalocyanine and naphthalocyanines (GB 2343186) as dyes for indicating diseased tissue and as sensitizers for SDT or PDT. See also Alfheim et al., U.S. Pat. No. 6,498,945; Lawandy, U.S. Pat. No. 5,817,048; Iger, WO 1998/052610; Lewis et al., US 20090275548A1; and Wang et al., US 20190070296A1. However, to date no sonodynamic therapy has been approved by regulatory agencies for use in humans.

BRIEF SUMMARY

Provided herein is a safe and effective sonodynamic therapy.

One aspect is a method for selectively inducing a directly cytotoxic effect within malignant tissue in a subject, the method comprising: providing an effective amount of 5-aminolevulinic acid to the malignant tissue; and exposing the tissue to ultrasound energy ("sonicating") using a focused ultrasound device, at a frequency of about 0.1 MHz to about 3 MHz, at an intensity at the ultrasound beam focus of about 3 W/cm$^2$ to about 100 W/cm$^2$.

Another aspect is a method for selectively inducing apoptosis within malignant tissue in a subject, the method comprising: providing an effective amount of 5-aminolevulinic acid to the malignant tissue; and sonicating the tissue to ultrasound energy using a focused ultrasound device, at a frequency of about 0.1 MHz to about 3 MHz, at an intensity at the ultrasound beam focus of about 3 W/cm$^2$ to about 100 W/cm$^2$.

Another aspect is a dosage form for use with a FUS device in the treatment of a subject in need of treatment, the dosage form comprising a container, comprising an effective amount of 5-aminolevulinic acid sufficient to treat the subject; and a machine-readable identifier readable by the FUS device, wherein the machine-readable identifier identifies the source of the 5-aminolevulinic acid, the amount of 5-aminolevulinic acid, the subject for which the 5-aminolevulinic acid has been prescribed, the FUS treatment parameters prescribed for the subject, an identification code or serial number, or a combination thereof.

Another aspect is A system for treating malignant tissue in a subject, the system comprising: an effective amount of 5-aminolevulinic acid; and a focused ultrasound (FUS) device.

DETAILED DESCRIPTION

One aspect is a method for selectively inducing a directly cytotoxic effect within malignant tissue in a subject, by providing an effective amount of 5-aminolevulinic acid to the malignant tissue; and exposing the tissue to ultrasound energy ("sonicating") using a focused ultrasound device, at a frequency of about 0.1 MHz to about 3 MHz, at an intensity at the ultrasound beam focus of about 3 W/cm$^2$ to about 100 W/cm$^2$. Directly cytotoxic effects include induction of apoptosis, necrosis, and/or physical destruction of cells. The effective amount of 5-ALA can be determined by standard methods. In general, the effective amount will be an amount sufficient to substantially stain the malignant tissue to be treated, without substantially staining normal tissue, or inducing an unacceptable level of toxicity. Without being bound by any particular theory, it is believed that sonicating tissue causes cavitation and microbubble generation, the collapse of which generate photons having wavelengths between about 300 nm and 700 nm within the tissue, and that these photons activate protoporphyrin-IX, leading to tissue destruction.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

All ranges disclosed herein also encompass any and all possible sub-ranges and combinations of sub-ranges thereof. Any listed range can be recognized as sufficiently describing and enabling the same range being broken down into at least equal halves, thirds, quarters, fifths, tenths, etc. As a non-limiting example, each range discussed herein can be readily broken down into a lower third, middle third and upper third, and so forth. As will also be understood by one skilled in the art all language such as "up to", "at least", "greater than", "less than", and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Malignant Tissue

Malignant tissue is typically tumorous or cancerous, but in general may be any type of tissue that is capable of taking up 5-ALA and accumulating protoporphyrin-IX, for example a benign tumor or other unwanted growth. Focused ultrasound is capable of passing through intervening tissue, which enables treatment of malignant tissue situated at otherwise inaccessible positions. For this reason, the methods of the disclosure are particularly useful for treating types of intracranial tumors, such as glioblastoma multiforme (including low grade and high grade glioblastomas), optical pathway gliomas, diffuse intrinsic pontine gliomas, astrocytoma, ependymoma, medulloblasoma, oligodendroglioma, hemangioblastoma, rhabdoid tumors, brain metastases from other cancers (including, for example without limitation, breast adenocarcinoma, small cell lung carcinoma, non-small cell lung carcinoma, squamous cell lung carcinoma, metastatic malignant melanoma, and prostate carcinoma), meningioma, primary pituitary gland malignancies, malignant nerve sheath tumors, and neurofibromas. Other malignant tissues include, without limitation, neoplasms, carcinomas, sarcomas, leukemias, lymphomas, and the like. Leukemias and lymphomas include, for example, cutaneous T-cell lymphoma (CTCL), noncutaneous peripheral T-cell lymphoma, lymphomas associated with human T-cell lymphotropic virus (HTLV), for example, adult T-cell leukemia/lymphoma (ATLL), acute lymphocytic leukemia, acute non-lymphocytic leukemias, chronic lymphocytic leukemia, chronic myelogenous leukemia, Hodgkin's Disease, non-Hodgkin's lymphomas, and multiple myeloma. Other tumors include, without limitation, childhood solid tumors such as brain tumors, neuroblastoma, retinoblastoma, Wilms' Tumor, bone tumors, and soft-tissue sarcomas; common solid tumors of adults such as head and neck cancers (e.g., infiltrating or metastatic squamous cell carcinoma, salivary gland tumors, nasopharyngeal carcinomas, oral, laryngeal, and esophageal tumors); genitourinary cancers (e.g., urethral, ureteral, renal cell, bladder carcinoma and bladder carcinoma in situ, locally advanced or metastatic carcinoma of the prostate, bladder, renal, uterine, ovarian, testicular, cancers, uterine, cervical, and uterine carcinoma), rectal, and colon cancer; lung cancer (including mesothelioma, small cell lung carcinoma, non-small cell lung carcinoma, squamous cell lung carcinoma); breast cancer; gastric, esophageal, and colon carcinoma, cholangiocarcinoma, hepatic carcinoma, and pancreatic adenocarcinoma; melanoma, infiltrating basal cell carcinomas, and other skin cancers; stomach cancer, brain cancer, liver cancer and thyroid cancer.

In some embodiments, the malignant tissue is glioblastoma multiforme, optical pathway glioma, diffuse intrinsic pontine glioma, astrocytoma, ependymoma, medulloblasoma, oligodendroglioma, hemangioblastoma, rhabdoid tumor, brain metastases from another cancers (such as breast adenocarcinoma, small cell lung carcinoma, non-small cell lung carcinoma, squamous cell lung carcinoma, metastatic malignant melanoma, or prostate carcinoma), meningioma, primary pituitary gland malignancy, malignant nerve sheath tumor, neurofibroma, cutaneous T-cell lymphoma (CTCL), noncutaneous peripheral T-cell lymphoma, lymphomas associated with human T-cell lymphotropic virus (HTLV), adult T-cell leukemia/lymphoma (ATLL), acute lymphocytic leukemia, acute nonlymphocytic leukemias, chronic lymphocytic leukemia, chronic myelogenous leukemia, Hodgkin's Disease, non-Hodgkin's lymphomas, multiple myeloma, neuroblastoma, retinoblastoma, Wilms' Tumor, bone tumors, soft-tissue sarcomas, infiltrating or metastatic squamous cell carcinoma, salivary gland tumors, nasopharyngeal carcinomas, oral, laryngeal, esophageal tumors, urethral cancer, ureteral cancer, renal cell cancer, bladder carcinoma, bladder carcinoma in situ, metastatic carcinoma of the prostate, bladder, renal, uterine, ovarian, testicular, cancers, uterine, cervical, and uterine carcinoma, rectal or colon cancer, lung cancer, mesothelioma, small cell lung carcinoma, non-small cell lung carcinoma, squamous cell lung carcinoma, breast cancer; gastric cancer, esophageal cancer, and colon carcinoma, cholangiocarcinoma, hepatic carcinoma, pancreatic adenocarcinoma, melanoma, infiltrating basal cell carcinomas, other skin cancers, liver cancer or thyroid cancer. In some embodiments, the malignant tissue is a glioblastoma multiforme, astrocytoma, ependymoma, medulloblastoma, oligodendroglioma, hemangioblastoma, or a rhabdoid tumor. In some embodiments, the malignant tissue is glioblastoma multiforme.

5-Aminolevulinic Acid

5-ALA can be provided in any pharmaceutically acceptable formulation, and may be provided as the free acid, a pharmaceutically acceptable salt, or a pharmaceutically acceptable ester. A formulation, Gliolan®, is commercially available.

Salts, esters, amides, prodrugs and other derivatives of the active agents can be prepared using standard procedures known to those skilled in the art of synthetic organic chemistry and described, for example, by March (1992) Advanced Organic Chemistry; *Reactions, Mechanisms and Structure,* 4th Ed. N.Y. Wiley-Interscience. Pharmaceutically acceptable salts are salts that retain the biological effectiveness and properties of the parent compound and which are not biologically or otherwise undesirable. 5-ALA is capable of forming acid and/or base salts by virtue of the presence of amino and/or carboxyl groups. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. Pharmaceutically acceptable esters include those obtained by replacing a hydrogen on an acidic group with an alkyl group, for example by reacting the acid group with an alcohol or a haloalkyl group. Examples of esters include, without limitation, those in which the hydrogen on an —C(O)OH group is replaced with an alkyl to form an —C(O)O-alkyl.

In some embodiments, the 5-ALA is sterilized by gamma irradiation (see U.S. Pat. No. 6,335,465, incorporated herein by reference in full). The 5-ALA formulation can be administered orally, intravenously, intrathecally, or intratumorally. In some embodiments, the 5-ALA is administered by intravenous administration. In some embodiments, gamma-irradiated 5-ALA is administered by intravenous administration. In some embodiments, the 5-ALA is administered at a dosage of at least about 1, 2, 3, 4, 5, 6, 7, 8, 9, 10, 12, 15, 20, 25, 30, 35, 40, 45, 50, 55, 60, 65, 70, 75, 80, 85, 90, 95, 96, 97, 98, 99, 100, 120, 125, 150, 175, 200, 300, 400, 500, 600, 750, or at least about 1000 mg/kg. In some embodiments, the 5-ALA is administered at a dosage of no more than about 1000, 900, 800, 700, 600, 500, 400, 300, 250, 200, 180, 175, 160, 150, 140, 130, 120, 110, 100, 90, 80, 70, 60, 50, 45, 40, 35, 30, 25, or 20 mg/kg. In some embodiments, 5-ALA is administered at a dosage of about 0.5 to about 250 mg/kg. In some embodiments, 5-ALA is administered at a dosage of 1 to 150 mg/kg. In some embodiments, 5-ALA is administered at a dosage of 5 to 90 mg/kg. In some embodiments, 5-ALA is administered at a dosage of 10 to 40 mg/kg.

Figure 1:
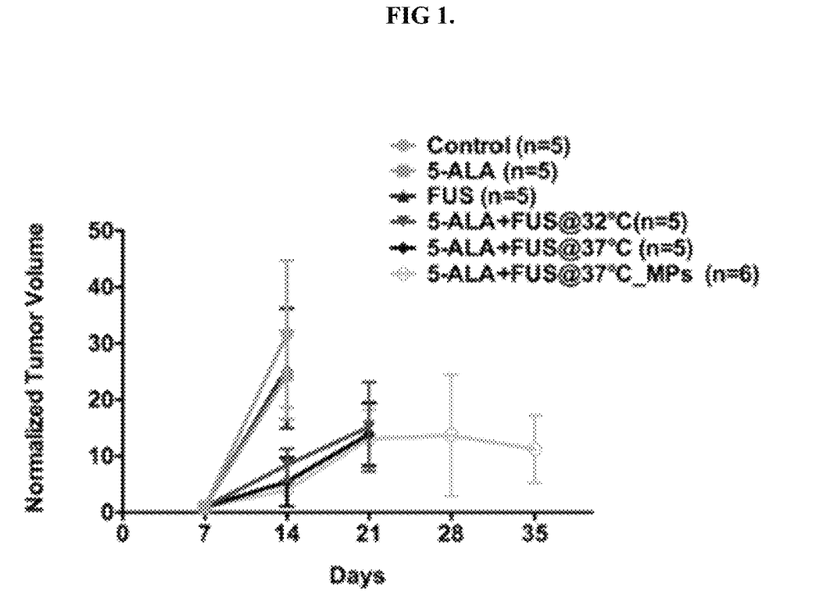
FIG. 1 shows the inhibition of implanted C6 glioma tumor growth in mice resulting from: (a) no treatment (solid circles); (b) treatment only with 5-ALA (squares); (c) treatment only with focused ultrasound (triangles); (d) treatment with 5-ALA and focused ultrasound, maximum brain temperature limited to 32° C. (inverted triangles); (e) treatment with 5-ALA and focused ultrasound, maximum brain temperature limited to 37° C. (diamonds); and (f) treatment with 5-ALA and focused ultrasound in 16 cycles (each 85 seconds on, 60 seconds rest), maximum brain temperature limited to 37° ° C. (open circles).
Figure 2:
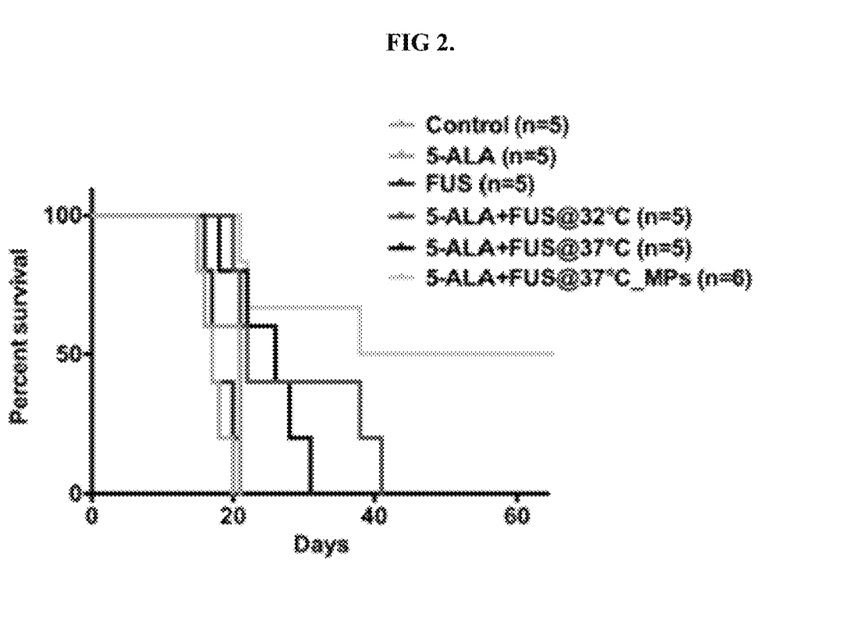
FIG. 2 shows the survival of mice with implanted C6 glioma tumor cells following: (a) no treatment; (b) treatment only with 5-ALA; (c) treatment only with focused ultrasound; (d) treatment with 5-ALA and focused ultrasound, maximum brain temperature limited to 32° C.; (e) treatment with 5-ALA and focused ultrasound, maximum brain temperature limited to 37° C.; and (f) treatment with 5-ALA and focused ultrasound at 16 multiple points, maximum brain temperature limited to 37° C.

The effective amount of 5-ALA required can be determined by standard methods known to those of skill in the art. For example, as described in Example 1 herein, one can implant tumor tissue into a mouse or other laboratory model subject, and treat the subject with different amounts of 5-ALA and FUS. As shown in FIG. 1, rats can be treated with 20 mg/kg of 5-ALA, then sonicated with 6.9 W/cm$^2$, 13.8 W/cm$^2$, 27.6 W/cm$^2$, or 55.2 W/cm$^2$ for 20 minutes. The results show that sonication at 13.8 W/cm$^2$ raised tumor temperature by about 2° C., to 32° C. Sonication at 27.6 W/cm$^2$ raised tumor temperature to about 37° C. Rats sonicated at 55.2 W/cm$^2$ suffered tissue damage. Untreated controls exhibited a normalized tumor volume of 32+10 mm$^3$, while 5-ALA only and FUS only groups exhibited a normalized tumor volume of 24+6 mm$^3$. All experimental groups exhibited inhibited tumor growth compared to control animals (see FIG. 1), and improved survival (see FIG. 2). The group that was sonicated at multiple points within the tumor (MP group) exhibited the greatest increase in survival, with 50% of the subjects surviving past 60 days. In some embodiments, the effective amount of 5-ALA is between 1 mg/kg and 1,000 mg/kg. In some embodiments, the effective amount of 5-ALA is between 5 mg/kg and 750 mg/kg. In some embodiments, the effective amount of 5-ALA is between 10 mg/kg and 750 mg/kg. In some embodiments, the effective amount of 5-ALA is between 20 mg/kg and 500 mg/kg. In some embodiments, the effective amount of 5-ALA is between 40 mg/kg and 500 mg/kg. In some embodiments, the effective amount of 5-ALA is between 10 mg/kg and 40 mg/kg. In some embodiments, the effective amount of 5-ALA is between 10 mg/kg and 20 mg/kg.

In some embodiments, an incubation period is included between administering 5-ALA and sonicating the malignant tissue, in order to allow sufficient time for 5-ALA to be taken up by the malignant tissue and converted to protoporphyrin-IX. In some embodiments, the incubation period is at least about 30 minutes, at least about one hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 18 hours, at least about 20 hours, or at least about 24 hours. In some embodiments, the incubation period is 72 hours, less than about 72 hours, less than about 60 hours, less than about 48 hours, less than about 36 hours, less than about 24 hours, less than about 22 hours, less than about 20 hours, less than about 18 hours, less than about 16 hours, less than about 15 hours, less than about 14 hours, less than about 13 hours, less than about 12 hours, less than about 11 hours, less than about 10 hours, less than about 9 hours, less than about 8 hours, less than about 7 hours, less than about 6 hours, less than about 5 hours, less than about 4 hours, or less than about 3 hours.

In some embodiments, the incubation period is between 1 and 72 hours. In some embodiments, the incubation period is between 2 and 48 hours. In some embodiments, the incubation period is between 3 and 36 hours. In some embodiments, the incubation period is between 4 and 24 hours. In some embodiments, the incubation period is between 4 and 18 hours. In some embodiments, the incubation period is between 4 and 24 hours. In some embodiments, the incubation period is between 4 and 18 hours. In some embodiments, the incubation period is about 6 hours.

Potentiating Agents

In some embodiments, the method further comprises administering a potentiating agent that enhances the therapeutic effect of 5-ALA, for example by promoting or increasing the uptake or accumulation of protoporphyrin-IX and/or 5-ALA, decreasing the rate at which protoporphyrin-IX and/or 5-ALA is metabolized, and the like. The potentiating agent can thus reduce the amount of 5-ALA required in order to obtain a given effect, or can increase the effect obtained from a given amount of 5-ALA, or any combination of desired effect and amount in between. Suitable potentiating agents include, for example without limitation, methotrexate, doxycycline, minocycline, Vitamin D3 and derivatives thereof. See, e.g., D.-F. Yang et al., *J Formos Med Assoc* (2014) 113(2):88-93; M.-J. Lee et al., *PLOS ONE* (2017) 12(5):e0178493; and E. V. Maytin et al., *Isr J Chem* (2012) 52(8-9):767-75. In some embodiments, the potentiating agent is selected from the group consisting of methotrexate, doxycycline, minocycline, Vitamin D3 and derivatives thereof. In some embodiments, the potentiating agent is methotrexate. In some embodiments, the potentiating agent is doxycycline. In some embodiments, the potentiating agent is minocycline. In some embodiments, the potentiating agent is Vitamin D3. In some embodiments, a combination of two or more potentiating agents is used. In some embodiments, a combination of two or more of methotrexate, doxycycline, minocycline, and Vitamin D3 is used.

The potentiating agent can be administered at the same time as 5-ALA, or at any other time prior to sonication. The optimal time for administering a potentiating agent can vary with the selection of potentiating agent or combination of agents. In some embodiments, the potentiating agent is administered at the same time as the 5-ALA. In some embodiments, the potentiating agent is administered in the same formulation as the 5-ALA. In some embodiments, the potentiating agent is administered at a different time. In some embodiments, the potentiating agent is administered prior to 5-ALA administration. In some embodiments, the potentiating agent is administered at least about 30 minutes, at least about one hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 18 hours, at least about 20 hours, at least about 24 hours, at least about 36 hours, at least about 48 hours, at least about 3 days, at least about 4 days, at least about 5 days, or at least about 6 days prior to the first sonication. In some embodiments, the potentiating agent is administered at 8 days, 7 days, 6 days, 5 days, 4 days, 84 hours, 72 hours, less than about 72 hours, less than about 60 hours, less than about 48 hours, less than about 36 hours, less than about 24 hours, less than about 22 hours, less than about 20 hours, less than about 18 hours, less than about 16 hours, less than about 15 hours, less than about 14 hours, less than about 13 hours, less than about 12 hours, less than about 11 hours, less than about 10 hours, less than about 9 hours, less than about 8 hours, less than about 7 hours, less than about 6 hours, less than about 5 hours, less than about 4 hours, or less than about 3 hours prior to the first sonication. In some embodiments, the potentiating agent administration period is between 1 and 72 hours prior to sonication. In some embodiments, the potentiating agent administration period is between 2 hours and 5 days prior to sonication. In some embodiments, the potentiating agent administration period is between 18 hours and 4 days prior to sonication. In some embodiments, the potentiating agent administration period is between 24 hours and 4 days prior to sonication. In some embodiments, the potentiating agent administration period is between 24 and 48 hours prior to sonication. In some embodiments, the potentiating agent administration period is between 48 and 96 hours prior to sonication. In some embodiments, the potentiating agent administration period is between 4 and 18 hours prior to sonication.

The amount of potentiating agent administered can be determined by those of skill in the art, and will in general depend on the potentiating agent or agents selected and the degree of potentiating effect to be obtained. Suitable methods include, for example without limitation, cell culture assays and/or in vivo experiments with model animals or explanted tissues to determine the degree of cell killing using varying amounts of 5-ALA and/or potentiating agents, with either sonication or photodynamic treatment. See, e.g., D.-F. Yang et al., *J Formos Med Assoc* (2014) 113(2):88-93; M.-J. Lee et al., *PLOS ONE* (2017) 12(5):e0178493; and E. V. Maytin et al., Isr *J Chem* (2012) 52(8-9):767-75.

The amount of potentiating agent used will be less than the amount at which unacceptable toxicity is experienced, and will be large enough to decrease the amount of 5-ALA required to obtain a potentiated effect. For example, one can determine the amount or number of malignant tissue or cells killed using a set amount of 5-ALA as a baseline for comparison, and then determine the amount or number of malignant tissue or cells killed using the same amount of 5-ALA in combination with different concentrations or amounts of the potentiating agent. Alternatively, one can determine the amount of 5-ALA needed to produce the same level of killing in the presence of different concentrations or amounts of the potentiating agent. The amount or number of malignant tissue or cells killed can be determined by cell counting, measurement of tumor volume, vital dye exclusion, and other techniques commonly used in medical research. The effect obtained with the potentiating agent will be an increase in effect or a decrease in 5-ALA dose of at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99% from the baseline measure. In some embodiments, the effect obtained with the potentiating agent is an increase in effect of at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 100, 120, 125, 150, 175, 200, 300, 400, or 500% from the baseline measure of degree of killing. In some embodiments, the effect obtained with the potentiating agent is a decrease in the amount of 5-ALA required to obtain the baseline killing rate of at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99%.

The amount of potentiating agent can be greater, equal, or less than the amount that is normally or typically prescribed for use of the potentiating agent alone. The upper limit is that amount at which unacceptable toxicity is experienced, either alone or in combination with 5-ALA. The lower limit is the amount needed to obtain a measurable potentiation effect, and can be 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 100, 120, 125, 150, 175, or 200% of the typical dose. For example without limitation, methotrexate can be administered as a single oral dose of about 7.5 mg to 10 mg between 24 hours and 72 hours prior to sonication; doxycycline can be administered BID at a dose of 100 mg, beginning with a 200 mg initial loading dose, starting two to four days prior to sonication; minocycline can be administered BID at a dose of 50 to 100 mg, starting two to four days prior to sonication; and Vitamin D3 can be administered as cholecalciferol at a dose of 10,000 to 100,000 IU/day for two to four days prior to sonication.

Microbubbles

Microbubbles (also known as microspheres) are gas-filled spheres having a diameter on the order of about 1 to 5 μm. They are sometimes used as contrast agents in medical sonography, as their echogenic properties help distinguish liquid-filled vessels from surrounding tissues. See, e.g., P. A. Dijkmans et al., *Eur J Cardiology* (2004) 5:245-56. The gas is often air, nitrogen, sulfur hexafluoride, or a perfluorocarbon such as, for example, octafluoropropane. The shell of the microbubble is often albumin, galactose, lipid, or a polymer. In an ultrasound acoustic field, microbubbles undergo linear oscillation at low power, and non-linear oscillation at higher power, leading to rupture at high power. The frequencies at which microbubbles resonate are determined primarily by the choice of gas in the core, and the mechanical properties of the shell. Mixtures of two or more different types of microbubbles can be used. In the practice of methods of the disclosure, microbubbles can be used to cause cavitation (and thus target cell death) at lower acoustic power than would otherwise obtain. In some embodiments, an effective amount of microbubbles is provided to the malignant tissue.

An effective amount of microbubbles is a quantity sufficient to increase the direct cytotoxic effect of 5-ALA and FUS on malignant tissue by at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 100, 120, 125, 150, 175, 200, 300, 400, or 500% from the baseline measure of degree of killing. Alternatively, the effective amount of microbubbles can be expressed as the quantity sufficient to decrease the 5-ALA dose and/or FUS dose by at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99% from the baseline measure.

Microbubbles can be prepared by methods known in the art, or can be obtained from commercial sources. Suitable microbubbles include, without limitation, enhanced contrast ultrasound microbubbles such as Definity® perflutren lipid microbubbles (Lantheus Medical Imaging, N. Billerica, MA), Levovist® lipid/galactose microspheres (Schering), Optison® microbubbles (GE Healthcare), and Lumason® microbubbles (Bracco Imaging (Monroe Township, NJ). In some embodiments, the microbubbles are enhanced contrast ultrasound microbubbles. In some embodiments, the microbubbles comprise sulfur hexafluoride or a perfluorocarbon. In some embodiments, the perfluorocarbon is octafluoropropane or perfluorohexane. In some embodiments, the microbubbles comprise air or nitrogen. In some embodiments, the microbubble shell comprises albumin. In some embodiments, the microbubbles are Definity® perflutren lipid microbubbles, Levovist® lipid/galactose microspheres, Optison® microbubbles, or Lumason® microbubbles.

Microbubbles can be administered together with 5-ALA and/or a potentiating agent, depending on the half-life of the microbubbles in the subject's system. In general, many microbubble agents have a very short half-life in human circulation, and accordingly are typically administered shortly before sonication. The quantity administered and the mode of administration is similar to the quantity and mode used by those of skill in the art when administering microbubbles for purposes of contrast-enhanced ultrasound sonography. The quantity administered will be at least 5, 10, 15, 20, 25, 30, 35, 40, 45, 50, 55, 60, 65, 70, 75, 80, 85, 90, 95, 100, 105, 110, 120, 140, 150, 160, 180, 200, 250, 300, 350, or 400% of the quantity used or recommended for use as a contrast-enhanced ultrasound sonography agent. The quantity administered will be no more than 500, 450, 400, 350, 300, 250, 200, 150, 100, 90, 80, 75, 70, 60, 50, 45, 40, 35, 30, 25, or 20% of the quantity used or recommended for use as a contrast-enhanced ultrasound sonography agent.

Focused Ultrasound

The malignant tissue is exposed to focused ultrasound energy ("sonicated") using a focused ultrasound (FUS) device. Suitable devices include the Exablate® Model 4000 Type-2 system (Insightec, Dallas, TX), and the like. The Type-2 has a dedicated 1000-element transducer which can operate in a sonication mode (i.e., a focused ultrasound pressure wave delivery mode) that uses low duration duty cycles to generate "burst sonication" at low power. This burst sonication mode enables the device to induce stable cavitation when used in conjunction with microbubbles at much lower energy levels than ultrasound-induced cavitation. The oscillation of the microbubbles induces a well targeted, temporary and reversible, but stable blood brain barrier disruption. The hallmark feature of the Exablate® device is its ability to monitor acoustic feedback in real-time to ensure a safe and effective BBB disruption. The Exablate® device is a magnetic resonance-guided focused ultrasound (MRgFUS) device, hence, it utilizes real time MR imaging to assess and monitor the safety of the procedure.

The ultrasound frequency is at least about 0.1 MHZ, at least about 0.2 MHz, at least about 0.25 MHz, at least about 0.3 MHZ, at least about 0.4 MHZ, at least about 0.45 MHz, at least about 0.5 MHz, at least about 0.55 MHz, at least about 0.6 MHz, at least about 0.65 MHz, at least about 0.7 MHz, at least about 0.75 MHz, at least about 0.8 MHz, at least about 0.85 MHz, at least about 0.9 MHZ, at least about 0.95 MHz, at least about 1 MHz, at least about 1.1 MHZ, at least about 1.5 MHz, at least about 2.0 MHz, at least about 2.1 MHZ, at least about 2.2 MHZ, at least about 2.3 MHZ, at least about 2.4 MHZ, at least about 2.5 MHz, at least about 2.75 MHz, at least about 3.0 MHz, at least about 3.5 MHz, at least about 4.0 MHz, at least about 4.5 MHz, at least about 5.0 MHz, at least about 6.0 MHz, at least about 7.0 MHz, at least about 8.0 MHZ, at least about 9.0 MHz, or at least about 10.0 MHz. The ultrasound frequency is no more than about 20 MHZ, no more than about 15 MHz, no more than about 10 MHz, no more than about 9.0 MHz, no more than about 8.0 MHz, no more than about 7.0 MHZ, no more than about 6.0 MHz, no more than about 5.0 MHz, no more than about 4.0 MHZ, no more than about 3.0 MHz, no more than about 2.8 MHz, no more than about 2.6 MHZ, no more than about 2.5 MHz, no more than about 2.4 MHz, no more than about 2.3 MHZ, no more than about 2.2 MHz, no more than about 2.1 MHz, or no more than about 2.0 MHz.

The focused ultrasound intensity, at the ultrasound beam focus, is at least about 1 W/cm$^2$, at least about 1.5 W/cm$^2$, at least about 2.0 W/cm$^2$, at least about 2.5 W/cm$^2$, at least about 3.0 W/cm$^2$, at least about 3.5 W/cm$^2$, at least about 4.0

W/cm², at least about 4.5 W/cm², at least about 5.0 W/cm², at least about 6.0 W/cm², at least about 7.0 W/cm², at least about 8.0 W/cm², at least about 9.0 W/cm², at least about 10.0 W/cm², at least about 15 W/cm², at least about 20 W/cm², at least about 25 W/cm², at least about 30 W/cm², at least about 35 W/cm², at least about 40 W/cm², at least about 45 W/cm², at least about 50 W/cm², at least about 60 W/cm², at least about 70 W/cm², at least about 75 W/cm², at least about 80 W/cm², at least about 90 W/cm², at least about 100 W/cm², at least about 120 W/cm², at least about 125 W/cm², at least about 130 W/cm², at least about 140 W/cm², at least about 145 W/cm², at least about 150 W/cm², or at least about 200 W/cm². The focused ultrasound intensity, at the ultrasound beam focus, is less than about 200 W/cm², less than about 150 W/cm², less than about 125 W/cm², less than about 100 W/cm², less than about 98 W/cm², less than about 95 W/cm², less than about 92 W/cm², less than about 90 W/cm², less than about 89 W/cm², less than about 88 W/cm², less than about 87 W/cm², less than about 86 W/cm², less than about 85 W/cm², less than about 84 W/cm², less than about 83 W/cm², less than about 82 W/cm², less than about 81 W/cm², less than about 80 W/cm², less than about 75 W/cm², less than about 70 W/cm², less than about 68 W/cm², less than about 67 W/cm², less than about 65 W/cm², less than about 66 W/cm², less than about 64 W/cm², less than about 63 W/cm², less than about 62 W/cm², less than about 61 W/cm², less than about 60 W/cm², less than about 58 W/cm², less than about 55 W/cm², less than about 54 W/cm², less than about 53 W/cm², less than about 52 W/cm², less than about 51 W/cm², less than about 50 W/cm², less than about 45 W/cm², less than about 40 W/cm², less than about 35 W/cm², or less than about 30 W/cm². In some embodiments, the focused ultrasound intensity is the spatial peak temporal average intensity (ISPTA).

The FUS energy applied during sonodynamic treatment is in general less than the amount of energy when using FUS to ablate tissue, and may be further reduced when microbubbles are administered prior to sonication. In some embodiments, the FUS energy applied is at least 10, 20, 30, 40, 50, 60, 70, 75, 80, 90, 100, 125, 150, 175, 200, 225, 250, 275, 300, 350, 400, 450, 500, 550, 600, 650, 700, 750, 800, 900, 1000, 1200, 1400, 1600, 1800, or 2000 Joules. In some embodiments, the FUS energy applied is no more than 5000, 4000, 3000, 2500, 2250, 2000, 1900, 1800, 1700, 1600, 1500, 1400, 1300, 1250, 1200, 1150, 1100, 1050, 1000, 950, 900, 850, 800, 750, 700, 650, 600, 550, 500, 450, 400, 350, 300, or 250 J. In some embodiments, the FUS energy applied is between 10 J and 2000 J. In some embodiments, the FUS energy applied is between 20 J and 1500 J. In some embodiments, the FUS energy applied is between 50 J and 1250 J. In some embodiments, the FUS energy applied is between 100 J and 1250 J. In some embodiments, the FUS energy applied is between 250 J and 1250 J. In some embodiments, the FUS energy applied is between 500 J and 1250 J.

The duration of sonication can vary depending on the subject, the particular type and stage of the malignant tissue, the location and amount of the malignant tissue, and the degree to which the malignant tissue takes up 5-ALA and accumulates protoporphyrin-IX. In some embodiments, the malignant tissue is sonicated at multiple points, for example, at multiple points within a tumor. As used herein, a "point" refers to an FUS focal point and the tissue surrounding the point that is affected by the FUS. By sonicating points distributed throughout the malignant tissue, one can achieve a more even and constant effect throughout the tumor volume. This also permits one to use a lower power, which reduces the possible rise in temperature (and with it, the possible risk to surrounding normal tissue). In some embodiments, malignant tissue is sonicated at individual points that together expose all of the malignant tissue to FUS. In some embodiments, the points overlap. The points can be sonicated simultaneously, individually, or in groups. For example, in a treatment that includes targeting 16 points, all 16 points can be sonicated simultaneously, or the points can be sonicated sequentially, or in a random order, or in groups such as, for example, in pairs or triplets, or groups of other sizes. Where groups are sonicated, the groups can be physically grouped, or distributed to non-adjacent regions. In some embodiments, the malignant tissue is sonicated at 1, 2, 3, 4, 5, 6, 7, 8, 9, 10, 11, 12, 15, 20, 25, or 30 individual points, or at any value from 1 to 30. In some embodiments, the malignant tissue is sonicated at no more than 30, 25, 20, 19, 18, 17, 16, 15, 14, 13, 12, 11, or 10 individual points.

In some embodiments, the sonication duration is at least about 20 seconds, at least about 30 seconds, at least about 45 seconds, at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 30 minutes, at least about 45 minutes, at least about 60 minutes, at least about 75 minutes, at least about 90 minutes, at least about 105 minutes, at least about 120 minutes, at least about 135 minutes, at least about 150 minutes, at least about 165 minutes, at least about 180 minutes, at least about 195 minutes, at least about 210 minutes, at least about 230 minutes, at least about 245 minutes, at least about 260 minutes, at least about 275 minutes, at least about 300 minutes, at least about 330 minutes, or at least about 360 minutes. In some embodiments, the sonication duration is less than about 360 minutes, less than about 330 minutes, less than about 300 minutes, less than about 290 minutes, less than about 280 minutes, less than about 270 minutes, less than about 260 minutes, less than about 250 minutes, less than about 240 minutes, less than about 230 minutes, less than about 220 minutes, less than about 210 minutes, less than about 200 minutes, less than about 195 minutes, less than about 190 minutes, less than about 185 minutes, less than about 180 minutes, less than about 170 minutes, less than about 160 minutes, less than about 150 minutes, less than about 140 minutes, less than about 130 minutes, less than about 120 minutes, less than about 110 minutes, less than about 100 minutes, less than about 90 minutes, less than about 80 minutes, less than about 70 minutes, less than about 60 minutes, less than about 50 minutes, less than about 40 minutes, less than about 30 minutes, less than about 20 minutes, or less than about 10 minutes.

The sonication can be continuous, or cyclic. In cyclic sonication, periods of exposure to focused ultrasound ("sonication periods") are interspersed with rest periods, with no sonication. In some embodiments, the sonication includes at least one rest period. In an embodiment, the sonication periods and rest periods are each independently at least about 5 seconds, at least about 10 seconds, at least about 15 seconds, at least about 20 seconds, at least about 25 seconds, at least about 30 seconds, at least about 35 seconds, at least about 40 seconds, at least about 45 seconds, at least about 50 seconds, at least about 55 seconds, at least about 60 seconds, at least about 65 seconds, at least about 70 seconds, at least about 75 seconds, at least about 80 seconds, at least about 85 seconds, at least about 90 seconds, at least about 95 seconds, at least about 100 seconds, at least about 105 seconds, at least about 110 seconds, at least about 115 seconds, at least about 120 seconds, at least about 125 seconds, at least about 130 seconds, at least about 140 seconds, at least about 150 seconds, at least about 160 seconds, at least about 165 seconds, at least about 170 seconds, at least about 175 seconds, or at least about 180 seconds. In an embodiment, the sonication periods and rest periods are each independently less than about 600 seconds, less than about 500 seconds, less than about 400 seconds, less than about 300 seconds, less than about 250 seconds, less than about 240 seconds, less than about 220 seconds, less than about 200 seconds, less than about 180 seconds, less than about 170 seconds, less than about 160 seconds, less than about 150 seconds, less than about 140 seconds, less than about 130 seconds, less than about 120 seconds, less than about 110 seconds, less than about 100 seconds, less than about 95 seconds, less than about 90 seconds, less than about 85 seconds, less than about 80 seconds, less than about 75 seconds, less than about 70 seconds, less than about 65 seconds, less than about 60 seconds, less than about 55 seconds, or less than about 50 seconds.

In the method of the disclosure, malignant tissue is selectively destroyed without affecting non-malignant tissue present at the ultrasound focus. In some embodiments, less than about 25%, less than about 20%, less than about 15%, less than about 10%, less than about 5%, less than about 4%, less than about 3%, less than about 2%, less than about 1% of the non-malignant tissue present at the ultrasound focus is damaged. In some embodiments, about 1%, about 2%, about 3%, about 4%, about 5%, about 10%, about 15%, about 20%, or about 25% of the non-malignant tissue present at the ultrasound focus is damaged. The amount of tissue damage can be determined using methods known to those of ordinary skill in the art, for example using MRI. In some embodiments, the temperature of the malignant tissue is raised by no more than 15° C., no more than 14° C., no more than 13° C., no more than 12° C., no more than 11° C., no more than 10° C., no more than 9° C., no more than 8° C., no more than 7° C., no more than 6° C., no more than 5° C., no more than 4° C., no more than 3° C., no more than 2° C., or no more than 1° C.

The ultrasound can be focused on the malignant tissue, or can be focused on a broader volume that includes the malignant tissue. Treatment with 5-ALA renders the malignant tissue more susceptible to FUS, making it possible to destroy malignant tissue without undue damage to non-malignant tissue included in the focus volume. For example, the tumor and a volume around it can be sonicated. Additionally, one can sonicate a complete anatomic region of the brain, such as, for example without limitation, a temporal lobe, a parietal lobe, a frontal lobe, an occipital lobe, the thalamus, the pituitary gland, the pons, the corpus callosum, the basal ganglia, the brainstem, an entire hemisphere, the supratentorial region, the infratentorial region, and the like. Additionally, one can sonicate a part or the whole of the brain FLAIR region (fluid-attenuated inversion recovery—an MRI technique designed to remove the signal from liquids in the brain). The methods of the disclosure can also in conjunction with surgical resection of a tumor, for example to treat the resulting tumor cavity to eliminate any malignant cells not removed by the resection.

In some embodiments, the position of the tumor is located using magnetic resonance imaging (MRI). In some embodiments, the tumor is located using X-ray imaging. In some embodiments, the tumor is sonicated. In some embodiments, the tumor and a volume around the tumor is sonicated. In some embodiments, the tumor and a margin extending from the tumor surface by 0.2, 0.5, 1, 2, 3, 4, 5, 6, 7, or 8 cm is sonicated. In some embodiments, a complete anatomic region of the brain undergoes sonication. In some embodiments, a temporal lobe, a parietal lobe, a frontal lobe, an occipital lobe, the thalamus, the pituitary gland, the pons, the corpus callosum, the basal ganglia, the brainstem, an entire hemisphere, the supratentorial region, or the infratentorial region is sonicated. In some embodiments, the brain FLAIR region is sonicated. In some embodiments, two or more anatomical regions are sonicated. In some embodiments, the tumor is resected, and the tumor cavity is sonicated to eliminate residual malignant tissue or cells. In some embodiments, the tumor cavity is sonicated to a depth of 0.2, 0.5, 1, 2, 3, 4, 5, 6, 7, or 8 cm.

In some embodiments, the method of the disclosure, including the administration of 5-ALA and sonication of malignant tissue, is repeated at a treatment interval or at least about 1 day, at least about 2 days, at least about 3 days, at least about 4 days, at least about 5 days, at least about 6 days, at least about 7 days, at least about 8 days, at least about 9 days, at least about 10 days, at least about 12 days, at least about 14 days, at least about 15 days, at least about 16 days, at least about 18 days, at least about 20 days, at least about 21 days, at least about 24 days, at least about 25 days, at least about 26 days, at least about 28 days, at least about 30 days, at least about 35 days, at least about 40 days, at least about 45 days, at least about 50 days, at least about 55 days, at least about 60 days, at least about 65 days, at least about 70 days, at least about 75 days, at least about 80 days, at least about 85 days, or at least about 90 days. In some embodiments, the treatment repetition interval is less than about 120 days, less than about 110 days, less than about 100 days, less than about 90 days, less than about 80 days, less than about 70 days, less than about 60 days, less than about 50 days, less than about 40 days, less than about 30 days, less than about 20 days, less than about 14 days, less than about 10 days, less than about 7 days, less than about 6 days, less than about 5 days, less than about 4 days, less than about 3 days, or less than about 2 days.

The subject of the disclosure is a mammal, which can be a human or a non-human mammal, for example a companion animal, such as a dog, cat, rat, or the like, or a farm animal, such as a horse, donkey, mule, goat, sheep, pig, or cow, and the like. In some embodiments, the subject is human.

Another aspect is the method for selectively inducing apoptosis within malignant tissue in a subject, by providing an effective amount of 5-aminolevulinic acid to the malignant tissue, and sonicating the tissue using a focused ultrasound device, at a frequency of about 0.1 MHz to about 3 MHz, at an intensity at the ultrasound beam focus of about 3 W/cm$^2$ to about 100 W/cm$^2$, using the methods and parameters set forth above.

Dosage Forms and Systems

It can occur that sonication is performed by a person other than a treating physician. In order to minimize risks, and insure that treatment is performed appropriately, one aspect is a dosage form for keying the focused ultrasound device operation to the subject to be treated. In some embodiments, the 5-ALA formulation is provided in a container that comprises a machine-readable identifier, wherein the identifier identifies the contents of the container, the source of the formulation, the amount of the formulation, the subject to which the formulation is to be administered, the focused ultrasound treatment prescribed for the subject (for example, specifying the ultrasound frequency, power, energy, duration, or a combination thereof), an identification code or serial number, or a combination thereof. The machine-readable identifier can be encrypted, in order to preserve confidential patient information. In some embodiments, the container is sufficient to contain an effective amount of 5-aminolevulinic acid, an effective amount of a potentiating agent, and/or an effective amount of microbubbles. In some embodiments, the machine-readable identifier is a bar code, QR code, or RFID device. In some embodiments, the focused ultrasound device includes a device for reading the machine-readable identifier. In some embodiments, the machine-readable identifier is encrypted. In some embodiments, the FUS device is locked in the absence of an appropriate machine-readable identifier. In some embodiments, the FUS device treatment parameters are programed via the machine-readable identifier.

SPECIFIC EMBODIMENTS

In some embodiments, provided is a method for selectively inducing a directly cytotoxic effect within malignant tissue in a subject, the method comprising providing an effective amount of 5-aminolevulinic acid, or a pharmaceutically acceptable salt or ester thereof, to the malignant tissue; and exposing the tissue to ultrasound energy ("sonicating") using a focused ultrasound device, at a frequency of about 0.1 MHz to about 3 MHz, at an intensity at the ultrasound beam focus of about 3 $W/cm^2$ to about 100 $W/cm^2$.

In some embodiments, provided is a method for selectively inducing apoptosis within malignant tissue in a subject, the method comprising providing an effective amount of 5-aminolevulinic acid, or a pharmaceutically acceptable salt or ester thereof, to the malignant tissue; and exposing the tissue to ultrasound energy ("sonicating") using a focused ultrasound device, at a frequency of about 0.1 MHz to about 3 MHz, at an intensity at the ultrasound beam focus of about 3 $W/cm^2$ to about 100 $W/cm^2$.

In some embodiments, the 5-aminolevulinic acid is gamma-irradiated 5-amino-levulinic acid. In an embodiment, the malignant tissue is exposed to ultrasound for a duration of about 1 min to about 6 hours. In an embodiment, the malignant tissue is exposed to ultrasound for a duration of about 1 min to about 180 min.

In some embodiments, the intensity is from about 5 $W/cm^2$ to about 80 $W/cm^2$. In some embodiments, the intensity is from about 5 $W/cm^2$ to about 60 $W/cm^2$. In an embodiment, the intensity is from about 5 $W/cm^2$ to about 50 $W/cm^2$. In some embodiments, the energy applied at the focus is between 10 J and 2000 J. In some embodiments, the energy applied at the focus is between 10 J and 2000 J.

In an embodiment, there is an incubation period between providing 5-aminolevulinic acid and soniciating the malignant tissue. In some embodiments, the incubation period is from about 1 hour to about 72 hours. In some embodiments, the incubation period is about 3 hours.

In some embodiments, the malignant tissue comprises tumor tissue. In some embodiments, the tumor tissue comprises glioblastoma multiforme, optical pathway glioma, diffuse intrinsic pontine glioma, astrocytoma, ependymoma, medulloblasoma, oligodendroglioma, hemangioblastoma, rhabdoid tumor, brain metastases from another cancer (selected from breast adenocarcinoma, small cell lung carcinoma, non-small cell lung carcinoma, squamous cell lung carcinoma, metastatic malignant melanoma, and prostate carcinoma), meningioma, primary pituitary gland malignancy, malignant nerve sheath tumor, neurofibroma, cutaneous T-cell lymphoma (CTCL), noncutaneous peripheral T-cell lymphoma, lymphomas associated with human T-cell lymphotropic virus (HTLV), adult T-cell leukemia/lymphoma (ATLL), acute lymphocytic leukemia, acute nonlymphocytic leukemias, chronic lymphocytic leukemia, chronic myelogenous leukemia, Hodgkin's Disease, non-Hodgkin's lymphomas, multiple myeloma, neuroblastoma, retinoblastoma, Wilms' Tumor, bone tumors, soft-tissue sarcomas, infiltrating or metastatic squamous cell carcinoma, salivary gland tumors, nasopharyngeal carcinomas, oral, laryngeal, esophageal tumors, urethral cancer, ureteral cancer, renal cell cancer, bladder carcinoma, bladder carcinoma in situ, metastatic carcinoma of the prostate, bladder, renal, uterine, ovarian, testicular, cancers, uterine, cervical, and uterine carcinoma, rectal or colon cancer, lung cancer, mesothelioma, small cell lung carcinoma, non-small cell lung carcinoma, squamous cell lung carcinoma, breast cancer, gastric cancer, esophageal cancer, and colon carcinoma, cholangiocarcinoma, hepatic carcinoma, pancreatic adenocarcinoma, melanoma, infiltrating basal cell carcinomas, other skin cancers, liver cancer or thyroid cancer.

In an embodiment, the tumor tissue comprises glioblastoma. In an embodiment, the malignant tissue is sonicated at multiple individual points. In some embodiments, the malignant tissue is located by magnetic resonance imaging prior to sonicating.

In some embodiments, the tissue sonicated comprises malignant tissue and non-malignant tissue. In some embodiments, the tissue sonicated comprises malignant tissue and a margin around the malignant tissue. In some embodiments, the outer edge of the margin is 0.2 cm to 5 cm from the malignant tissue. In some embodiments, the outer edge of the margin is 1 cm to 3 cm from the malignant tissue. In some embodiments, the tissue sonicated comprises a margin around a resection location after resection of malignant tissue. In some embodiments, the outer edge of the margin is 0.2 cm to 5 cm from the malignant tissue resection site.

In some embodiments, the tissue sonicated comprises a complete anatomic region of the brain. In some embodiments, the complete anatomic region of the brain is a temporal lobe, a parietal lobe, a frontal lobe, an occipital lobe, the thalamus, the pituitary gland, the pons, the corpus callosum, the basal ganglia, the brainstem, a hemisphere, the supratentorial region, or the infratentorial region. In some embodiments, the complete anatomic region of the brain is the brain FLAIR region.

In an embodiment, less than about 25% of the non-malignant tissue in the ultrasound beam focus is damaged. In an embodiment, less than about 10% of the non-malignant tissue in the ultrasound beam focus is damaged. In an embodiment, less than about 5% of the non-malignant tissue in the ultrasound beam focus is damaged. In some embodiments, the temperature of the malignant tissue is raised by sonication by no more than about 10° C. In some embodiments, the temperature of the malignant tissue is raised by sonication by no more than about 5° C. In some embodiments, the temperature of the malignant tissue is raised by sonication by no more than about 2° C.

In some embodiments, the subject is human. In some embodiments, the 5-aminolevulinic acid is provided to the malignant tissue by oral administration of an oral formulation or intravenous administration of an i.v. formulation to the subject. In some embodiments, the 5-aminolevulinic acid is provided to the malignant tissue by intravenous administration to the subject.

In some embodiments, the method further comprises providing an effective amount of a 5-ALA potentiating agent to the malignant tissue. In some embodiments, the potentiating agent is selected from the group consisting of doxycycline, methotrexate, minocycline, and Vitamin D3 or a derivative thereof. In some embodiments, the method further comprises providing an effective amount of microbubbles to the malignant tissue. In some embodiments, the microbubbles are enhanced contrast ultrasound microbubbles. In some embodiments, the microbubbles comprise sulfur hexafluoride or a perfluorocarbon.

In some embodiments, the 5-aminolevulinic acid is provided in a container, the container further comprising a machine-readable identifier, wherein the machine-readable identifier identifies the source of the 5-aminolevulinic acid, the amount of 5-aminolevulinic acid, the subject to which the 5-aminolevulinic acid is to be administered, the focused ultrasound treatment parameters prescribed for the subject, an identification code or serial number, or a combination thereof. In some embodiments, the focused ultrasound treatment parameters comprise the ultrasound frequency, power, energy, duration, or a combination thereof. In some embodiments, the focused ultrasound device comprises a scanning element capable of scanning the machine-readable identifier, wherein the treatment parameters of the focused ultrasound device are set in response to the machine-readable identifier. In some embodiments, the focused ultrasound device is locked in the absence of a machine-readable identifier.

In some embodiments, the effective amount of 5-ALA is between about 1 mg/kg body weight and 1000 mg/kg body weight. In some embodiments, the effective amount of 5-ALA is between about 10 mg/kg body weight and 750 mg/kg body weight. In some embodiments, the effective amount of 5-ALA is between about 20 mg/kg body weight and 500 mg/kg body weight.

In some embodiments, steps a) through b) are repeated at a treatment interval of about 1 day to about 60 days. In some embodiments, the ultrasound exposure duration comprises at least one rest period. In some embodiments, the ultrasound exposure duration comprises rest periods of about 10 seconds to about 120 seconds, separated by sonication periods of about 10 seconds to about 180 seconds. In some embodiments, the sonication periods are about 60 to about 90 seconds, and the rest periods are about 45 to about 75 seconds.

In some embodiments, provided is a dosage form for use with a FUS device in the treatment of a subject in need of treatment, the dosage form comprising a container, comprising an effective amount of 5-aminolevulinic acid sufficient to treat the subject; and a machine-readable identifier readable by the FUS device, wherein the machine-readable identifier identifies the source of the 5-aminolevulinic acid, the amount of 5-aminolevulinic acid, the subject for which the 5-aminolevulinic acid has been prescribed, the FUS treatment parameters prescribed for the subject, an identification code or serial number, or a combination thereof. In some embodiments, the machine-readable identifier is encrypted, and comprises information for automatically programming the FUS.

In some embodiments, provided is a system for treating malignant tissue in a subject, the system comprising an effective amount of 5-aminolevulinic acid; and a focused ultrasound (FUS) device. In some embodiments, the system further comprises an effective amount of a potentiating agent and/or an effective amount of microbubbles. In some embodiments, the system further comprises a container sufficient to contain the effective amount of 5-aminolevulinic acid, an effective amount of a potentiating agent, and/or an effective amount of microbubbles; wherein the container comprises a machine-readable identifier readable by the FUS device, wherein the machine-readable identifier identifies the source of the 5-aminolevulinic acid, the amount of 5-aminolevulinic acid, the subject for which the 5-aminolevulinic acid has been prescribed, the FUS treatment parameters prescribed for the subject, an identification code or serial number, or a combination thereof. In some embodiments, the machine-readable identifier is encrypted, and comprises information for automatically programming the FUS. In some embodiments, the FUS is locked in the absence of the machine-readable identifier. In some embodiments, the FUS device is a magnetic resonance-guided FUS device (MRgFUS).

EXAMPLES

The following preparations and examples are given to enable those skilled in the art to more clearly understand and to practice the present invention. They should not be considered as limiting the scope of the invention, but merely as being illustrative and representative thereof.

Example 1

Treatment Procedure

Male Wistar rats received injections of $4 \times 10^5$ C6 glioma tumor cells by injection into the right cortex of the brain. On day 7 after injection, rats were administered 5-aminolevulinic acid (20 mg/kg or 0 mg/kg, Levulan®, DUSA Pharmaceuticals, Wilmington, MA) orally, three hours prior to treatment.

Rats were anesthetized and set inside an MRI-guided focused ultrasound system ("FUS", RK300, FUS Instruments, Toronto, Canada), having a 25 mm diameter spherically curved transducer (resonant frequency $f_0$=1.06 MHz, focal number=0.8). The FUS, with rat, was then inserted into a 7 Telsa MRI system (Brucker BioSpec 70/30 USR, Bruker Ltd., Milton, Ontario, Canada). The MRI was used to precisely aim the FUS device at the brain tumor. Rats were then sonicated at one of four spatial peak temporal average intensities (ISPTA) (6.9 W/cm$^2$, 13.8 W/cm$^2$, 27.6 W/cm$^2$, or 55.2 W/cm$^2$) for 20 minutes. One group (N=6) was cyclicly sonicated at 27.6 W/cm$^2$ for 20 minutes, divided into 16 sonication periods of 85 seconds, separated by rest periods of 60 seconds (the multiple point, or "MP" group). In the MP group, 16 individual points within the tumor were sonicated. Control groups (N=5 each) received 5-ALA without FUS treatment, FUS treatment without 5-ALA, or neither 5-ALA nor FUS. Tumor temperature was monitored during sonication using magnetic resonance thermometry. Normalized tumor volume was measured by MRI on days 7, 14, 21, 28, and 35 following injection.

Results

Sonication at 13.8 W/cm$^2$ raised tumor temperature by about 2° C., to 32° C. Sonication at 27.6 W/cm$^2$ raised tumor temperature to about 37° C. Rats sonicated at 55.2 W/cm$^2$ suffered tissue damage and were euthanized. Untreated controls exhibited a normalized tumor volume of 32+10 mm$^3$, while 5-ALA only and FUS only groups exhibited a normalized tumor volume of 24+6 mm$^3$. All experimental groups exhibited inhibited tumor growth (see FIG. 1), and improved survival (see FIG. 2). The MP group exhibited the greatest increase in survival.

Example 2

This experiment is performed to demonstrate safety and tolerability of treatment with 5-ALA and MRgFUS.

Treatment Procedure

Human subjects are selected meeting the following criteria: (a) presence of recurrent glioma (WHO grade 3 or 4); (b) prior treatment using the Stupp protocol; and (c) planned resection of the tumor. The Stupp protocol is radiotherapy of 2 Gy Monday through Friday for six weeks, totaling 60 Gy, with temozolomide (75 mg/m² body surface area) daily for the six weeks of radiotherapy, followed by six cycles of temozolomide (150-200 mg/m²) for 5 days each 28 day cycle after completion of radiotherapy (R. Stupp et al., *New Engl J Med* (2005) 352:987-96).

Each subject is treated with intravenous 5-ALA and MRgFUS at the amounts set forth in Table 1 below, at 2 to 4 weeks prior to the subject's planned craniotomy. In each subject, the FUS is focused on one half of the tumor, including enhancing and non-enhancing regions. The treatment is performed first with dose level 1, and the subjects are examined for dose limiting toxicities (DLT). If no DLTs are observed, the next cohort of subjects is treated at dose level 2. This escalation is repeated for each cohort unless a DLT is observed. If one DLT is observed, the dose level is repeated with the next cohort, with an expansion of additional three subjects. If two or more DLTs are observed, the prior dose level is designated as the maximum tolerated dose.

TABLE 1

Dose Levels

| Dose Level | 5-ALA (mg/kg) | FUS (Joules) |
|---|---|---|
| 1 | 10 | 250 |
| 2 | 10 | 500 |
| 3 | 10 | 1000 |
| 4 | 20 | 250 |
| 5 | 20 | 500 |
| 6 | 20 | 1000 |
| 7 | 40 | 250 |
| 8 | 40 | 500 |
| 9 | 40 | 1000 |

Results

The tumor is monitored by MRI or X-ray imaging periodically prior to resection. Following resection of the tumor, the resected tumor is examined for differences between the sonicated and non-sonicated halves, including any reduction in size or grade of the tissue.

The discussion of the general methods given herein is intended for illustrative purposes only. Other alternative methods and alternatives will be apparent to those of skill in the art upon review of this disclosure, and are to be included within the spirit and purview of this application.

Throughout this specification, various patents, patent applications and other types of publications (e.g., journal articles, electronic database entries, etc.) are referenced. The disclosure of all patents, patent applications, and other publications cited herein are hereby incorporated by reference in their entirety to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

What is claimed is:

1. A method for treating diffuse intrinsic pontine glioma in a human subject in need thereof, the method comprising:
   a) intravenously administering from 5 mg/kg to 750 mg/kg of gamma-irradiated 5-aminolevulinic acid (5-ALA), or a pharmaceutically acceptable salt thereof, to the subject; and
   b) exposing diffuse intrinsic pontine glioma tissue in the subject to ultrasound energy by sonicating the tissue at a plurality of individual points using a focused ultrasound (FUS) device at a frequency of about 0.1 MHz to about 3 MHz and an intensity at an ultrasound beam focus of about 3 W/cm² to about 100 W/cm².

2. The method of claim 1, wherein the tissue is exposed to the ultrasound for a duration of about 1 min to about 6 hours.

3. The method of claim 2, wherein the ultrasound exposure duration comprises at least one rest period.

4. The method of claim 3, wherein the ultrasound exposure duration comprises rest periods of about 10 seconds to about 120 seconds, separated by sonication periods of about 10 seconds to about 180 seconds.

5. The method of claim 4, wherein the sonication periods are about 60 to about 90 seconds, and the rest periods are about 45 to about 75 seconds.

6. The method of claim 1, wherein the tissue is exposed to the ultrasound for a duration of about 1 min to about 180 min.

7. The method of claim 1, wherein the intensity is from about 5 W/cm² to about 80 W/cm².

8. The method of claim 1, wherein the energy applied at the focus is between 10 J and 2000 J.

9. The method of claim 1, wherein there is an incubation period between administering the 5-ALA and sonicating the tissue.

10. The method of claim 9, wherein the incubation period is from about 1 hour to about 72 hours.

11. The method of claim 9, wherein the incubation period is about 6 hours.

12. The method of claim 1, wherein the tissue is sonicated at from 2 to 30 individual points.

13. The method of claim 1, further comprising locating the tissue by magnetic resonance imaging prior to the sonicating.

14. The method of claim 1, wherein the tissue sonicated comprises malignant tissue and non-malignant tissue.

15. The method of claim 14, wherein the tissue sonicated comprises the malignant tissue and a margin around the malignant tissue.

16. The method of claim 15, wherein an outer edge of the margin is 0.2 cm to 5 cm from the malignant tissue.

17. The method of claim 16, wherein the outer edge of the margin is 1 cm to 3 cm from the malignant tissue.

18. The method of claim 14, wherein less than about 25% of the non-malignant tissue in the ultrasound beam focus is damaged.

19. The method of claim 1, wherein the tissue sonicated comprises a complete anatomic region of a brain.

20. The method of claim 19, wherein the complete anatomic region of the brain is a temporal lobe, a parietal lobe, a frontal lobe, an occipital lobe, a thalamus, a pituitary gland, a pons, a corpus callosum, a basal ganglia, a brainstem, a hemisphere, a supratentorial region, or an infratentorial region.

21. The method of claim 1, wherein the tissue sonicated comprises a pons.

22. The method of claim 1, wherein a temperature of the malignant tissue is raised by sonication no more than about 10° C.

23. The method of claim 1, wherein a temperature of the tissue is raised by sonication no more than about 5° C.

24. The method of claim 1, wherein a temperature of the tissue is raised by sonication no more than about 2° C.

25. The method of claim 1, further comprising providing an effective amount of microbubbles to the tissue.

26. The method of claim 25, wherein the microbubbles are enhanced contrast ultrasound microbubbles.

27. The method of claim 1, comprising intravenously administering 5 mg/kg 5-ALA.

28. The method of claim 1, comprising intravenously administering 10 mg/kg 5-ALA.

29. The method of claim 1, wherein steps a) through b) are repeated at a treatment interval of at least about 21 days and less than about 30 days.

* * * * *